(12) United States Patent
Ducharme

(10) Patent No.: US 9,101,744 B2
(45) Date of Patent: Aug. 11, 2015

(54) SYSTEMS AND METHODS FOR DELIVERING THERAPEUTIC AGENTS

(71) Applicant: COOK MEDICAL TECHNOLOGIES LLC, Bloomington, IN (US)

(72) Inventor: Richard W Ducharme, Alexandria, PA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 13/725,206

(22) Filed: Dec. 21, 2012

(65) Prior Publication Data

US 2013/0110080 A1 May 2, 2013

Related U.S. Application Data

(63) Continuation-in-part of application No. 13/351,524, filed on Jan. 17, 2012, which is a continuation of application No. 12/787,796, filed on May 26, 2010, now Pat. No. 8,118,777.

(60) Provisional application No. 61/182,463, filed on May 29, 2009.

(51) Int. Cl.
*A61M 1/00* (2006.01)
*A61M 13/00* (2006.01)
*A61M 37/00* (2006.01)
(Continued)

(52) U.S. Cl.
CPC ........... *A61M 37/0069* (2013.01); *A61M 5/155* (2013.01); *A61M 11/02* (2013.01); *A61M 37/00* (2013.01); *A61M 5/2053* (2013.01)

(58) Field of Classification Search
CPC ..... A61M 11/02; A61M 31/00; A61M 37/00; A61M 37/0069; A61M 5/155; A61M 5/2053
USPC .......................................................... 604/118
See application file for complete search history.

(56) References Cited

U.S. PATENT DOCUMENTS

| 39,678 A | 8/1863 | Russell |
| 170,182 A | 11/1875 | Molesworth |

(Continued)

FOREIGN PATENT DOCUMENTS

| CH | 15244 A | 9/1897 |
| CH | 257250 A | 3/1949 |

(Continued)

OTHER PUBLICATIONS

Office Action dated Aug. 4, 2010 for U.S. Appl. No. 12/435,574, 7 pgs.

(Continued)

*Primary Examiner* — Jason Flick
(74) *Attorney, Agent, or Firm* — Brinks Gilson & Lione

(57) ABSTRACT

The present embodiments provide systems and methods suitable for delivering a therapeutic agent to a target site. The systems generally comprise a container having first and second regions and a reservoir containing the therapeutic agent. A pressure source having pressurized fluid is in selective fluid communication with at least a portion of the reservoir. An outlet tube is in fluid communication with the reservoir of the container. At least one slot is formed in a lateral surface of the outlet tube at a position between first and second ends of the outlet tube.

20 Claims, 7 Drawing Sheets

(51) Int. Cl.
*A61M 5/155* (2006.01)
*A61M 11/02* (2006.01)
*A61M 5/20* (2006.01)

(56) References Cited

U.S. PATENT DOCUMENTS

| | | | |
|---|---|---|---|
| 442,785 A | 12/1890 | Schoettl |
| 460,458 A | 9/1891 | Bates |
| 471,865 A | 3/1892 | Howard |
| 533,489 A | 2/1895 | Ogram |
| 566,411 A | 8/1896 | Schoene |
| 576,437 A | 2/1897 | Elliot |
| 693,587 A | 2/1902 | Campbell |
| 775,985 A | 11/1904 | McKain |
| 881,238 A | 3/1908 | Hasbrouck |
| 904,149 A | 11/1908 | Rachmann |
| 938,648 A | 11/1909 | DeVilbiss |
| 1,022,601 A | 4/1912 | Rumberg et al. |
| 1,114,114 A | 10/1914 | Cochenour |
| 1,145,520 A | 7/1915 | Smith |
| 1,261,503 A | 4/1918 | Figgis |
| 1,357,452 A | 11/1920 | Hall |
| 1,466,119 A | 8/1923 | Claflin |
| 1,521,396 A | 12/1924 | Scott |
| 1,685,280 A | 9/1928 | Findley |
| 1,934,793 A | 11/1933 | Crain et al. |
| 2,004,402 A | 6/1935 | Conklin |
| 2,151,418 A | 3/1939 | Bolte |
| 2,223,611 A | 12/1940 | Gross |
| 2,307,986 A | 1/1943 | Bolte et al. |
| 2,390,313 A | 12/1945 | Macgill |
| 2,507,702 A | 5/1950 | Fields |
| 2,519,555 A | 8/1950 | Fields |
| 2,609,155 A | 9/1952 | Fosnaugh |
| 2,632,444 A | 3/1953 | Kas |
| 2,805,013 A | 9/1957 | Cordis |
| 2,934,314 A | 4/1960 | Chambers et al. |
| 2,956,579 A | 10/1960 | Moore et al. |
| 3,016,895 A | 1/1962 | Sein et al. |
| 3,050,261 A | 8/1962 | Littlefield |
| 3,506,008 A | 4/1970 | Huck |
| 3,540,444 A | 11/1970 | Moreland |
| 3,572,335 A | 3/1971 | Robinson |
| 3,589,363 A | 6/1971 | Banko et al. |
| 3,599,866 A | 8/1971 | Bolton |
| 3,632,046 A | 1/1972 | Hengesbach |
| 3,647,143 A | 3/1972 | Gauthier et al. |
| 3,649,299 A | 3/1972 | Sholl |
| 3,667,465 A | 6/1972 | Voss |
| 3,710,400 A | 1/1973 | Sparks |
| 3,742,955 A | 7/1973 | Battista et al. |
| 3,744,493 A | 7/1973 | Booher et al. |
| 3,762,410 A | 10/1973 | Bindel |
| 3,788,315 A | 1/1974 | Laurens |
| 3,815,595 A | 6/1974 | Bar |
| 3,900,022 A | 8/1975 | Widran |
| 3,916,896 A | 11/1975 | Ballard |
| 4,017,007 A | 4/1977 | Riccio |
| 4,040,420 A | 8/1977 | Speer |
| 4,174,811 A | 11/1979 | Binder et al. |
| 4,184,258 A | 1/1980 | Barrington et al. |
| 4,204,539 A | 5/1980 | Van Brugge |
| 4,204,645 A | 5/1980 | Hopp |
| 4,210,140 A | 7/1980 | James et al. |
| 4,359,049 A | 11/1982 | Redl et al. |
| 4,423,727 A | 1/1984 | Widran et al. |
| 4,427,650 A | 1/1984 | Stroetmann |
| 4,516,442 A | 5/1985 | Davis |
| 4,534,345 A | 8/1985 | Wetterlin |
| 4,539,716 A | 9/1985 | Bell |
| 4,578,067 A | 3/1986 | Cruz, Jr. |
| 4,606,501 A | 8/1986 | Bate et al. |
| 4,620,847 A | 11/1986 | Shishov et al. |
| 4,631,055 A | 12/1986 | Redl et al. |
| 4,637,816 A | 1/1987 | Mann |
| H257 H | 4/1987 | Barditch et al. |
| 4,655,211 A | 4/1987 | Sakamoto et al. |
| 4,735,616 A | 4/1988 | Eibl et al. |
| 4,738,658 A | 4/1988 | Magro et al. |
| 4,738,740 A | 4/1988 | Pinchuk |
| 4,752,466 A | 6/1988 | Saferstein et al. |
| 4,790,819 A | 12/1988 | Li et al. |
| 4,798,606 A | 1/1989 | Pinchuk |
| 4,803,977 A | 2/1989 | Kremer, Jr. |
| 4,846,405 A | 7/1989 | Zimmermann |
| D303,139 S | 8/1989 | Morgan |
| 4,872,450 A | 10/1989 | Austad |
| 4,874,368 A | 10/1989 | Miller et al. |
| 4,890,612 A | 1/1990 | Kensey |
| 4,900,303 A | 2/1990 | Lemelson |
| 4,902,278 A | 2/1990 | Maget et al. |
| 4,902,281 A | 2/1990 | Avoy |
| 4,927,410 A | 5/1990 | Kovacs |
| 4,929,246 A | 5/1990 | Sinofsky |
| 4,941,874 A | 7/1990 | Sandow et al. |
| 4,941,880 A | 7/1990 | Burns |
| 4,945,050 A | 7/1990 | Sanford et al. |
| 4,946,870 A | 8/1990 | Partain, III. et al. |
| 4,950,234 A | 8/1990 | Fujioka et al. |
| 4,969,874 A | 11/1990 | Michel et al. |
| 4,978,336 A | 12/1990 | Capozzi et al. |
| 4,994,028 A | 2/1991 | Leonard et al. |
| 5,009,637 A | 4/1991 | Newman et al. |
| 5,015,580 A | 5/1991 | Christou et al. |
| 5,021,059 A | 6/1991 | Kensey et al. |
| 5,053,000 A | 10/1991 | Booth et al. |
| 5,059,187 A | 10/1991 | Sperry et al. |
| 5,061,180 A | 10/1991 | Wiele |
| 5,063,025 A | 11/1991 | Ito |
| 5,064,413 A | 11/1991 | McKinnon et al. |
| 5,106,370 A | 4/1992 | Stewart |
| 5,116,315 A | 5/1992 | Capozzi et al. |
| 5,120,657 A | 6/1992 | McCabe et al. |
| 5,129,825 A | 7/1992 | Discko, Jr. |
| 5,129,882 A | 7/1992 | Weldon et al. |
| 5,133,701 A | 7/1992 | Han |
| 5,141,515 A | 8/1992 | Eberbach |
| 5,147,292 A | 9/1992 | Kullas et al. |
| 5,149,655 A | 9/1992 | McCabe et al. |
| 5,165,604 A | 11/1992 | Copp, Jr. |
| 5,176,642 A | 1/1993 | Clement |
| 5,179,022 A | 1/1993 | Sanford et al. |
| D333,000 S | 2/1993 | Good et al. |
| 5,204,253 A | 4/1993 | Sanford et al. |
| 5,219,328 A | 6/1993 | Morse et al. |
| 5,226,567 A | 7/1993 | Sansalone |
| 5,226,877 A | 7/1993 | Epstein |
| 5,273,531 A | 12/1993 | Knoepfler |
| 5,292,309 A | 3/1994 | Van Tassel et al. |
| 5,310,407 A | 5/1994 | Casale |
| 5,312,333 A | 5/1994 | Churinetz et al. |
| 5,328,459 A | 7/1994 | Laghi |
| 5,391,183 A | 2/1995 | Janzen et al. |
| 5,392,992 A | 2/1995 | Farnsteiner et al. |
| 5,395,326 A | 3/1995 | Haber et al. |
| 5,405,607 A | 4/1995 | Epstein |
| 5,415,631 A | 5/1995 | Churinetz et al. |
| 5,429,278 A | 7/1995 | Sansalone |
| 5,445,612 A | 8/1995 | Terakura et al. |
| 5,447,499 A | 9/1995 | Allaire et al. |
| 5,469,994 A | 11/1995 | Reh et al. |
| 5,470,311 A | 11/1995 | Setterstrom et al. |
| 5,484,403 A | 1/1996 | Yoakum et al. |
| 5,503,623 A | 4/1996 | Tilton, Jr. |
| 5,520,658 A | 5/1996 | Holm |
| 5,538,162 A | 7/1996 | Reh et al. |
| 5,553,741 A | 9/1996 | Sancoff et al. |
| 5,558,646 A | 9/1996 | Roche |
| 5,582,596 A | 12/1996 | Fukunaga et al. |
| 5,584,807 A | 12/1996 | McCabe |
| 5,584,815 A | 12/1996 | Pawelka et al. |
| 5,601,603 A | 2/1997 | Illi |
| 5,605,541 A | 2/1997 | Holm |
| 5,612,050 A | 3/1997 | Rowe et al. |

(56) References Cited

U.S. PATENT DOCUMENTS

| | | | |
|---|---|---|---|
| 5,665,067 | A | 9/1997 | Linder et al. |
| 5,697,947 | A | 12/1997 | Wolf et al. |
| 5,707,402 | A | 1/1998 | Heim |
| 5,749,968 | A | 5/1998 | Melanson et al. |
| 5,759,171 | A | 6/1998 | Coelho |
| 5,788,625 | A | 8/1998 | Plouhar et al. |
| 5,865,796 | A | 2/1999 | McCabe |
| 5,873,530 | A | 2/1999 | Chizinsky |
| 5,902,228 | A | 5/1999 | Schulsinger et al. |
| 5,919,184 | A | 7/1999 | Tilton, Jr. |
| 5,951,531 | A | 9/1999 | Ferdman et al. |
| 6,007,515 | A | 12/1999 | Epstein et al. |
| 6,013,050 | A | 1/2000 | Bellhouse et al. |
| 6,021,776 | A | 2/2000 | Allred et al. |
| 6,027,471 | A | 2/2000 | Fallon et al. |
| 6,059,749 | A | 5/2000 | Marx |
| 6,077,217 | A | 6/2000 | Love et al. |
| 6,117,150 | A | 9/2000 | Pingleton et al. |
| 6,165,201 | A | 12/2000 | Sawhney et al. |
| 6,368,300 | B1 | 4/2002 | Fallon et al. |
| 6,394,975 | B1 | 5/2002 | Epstein |
| 6,454,786 | B1 | 9/2002 | Holm et al. |
| 6,461,325 | B1 | 10/2002 | Delmotte et al. |
| 6,461,361 | B1 | 10/2002 | Epstein |
| 6,478,754 | B1 | 11/2002 | Babaev |
| 6,537,246 | B1 | 3/2003 | Unger et al. |
| 6,610,026 | B2 | 8/2003 | Cragg et al. |
| 6,641,800 | B1 | 11/2003 | Mistry et al. |
| 6,689,108 | B2 | 2/2004 | Lavi et al. |
| 6,716,190 | B1 | 4/2004 | Glines et al. |
| 6,723,067 | B2 | 4/2004 | Nielson |
| 6,811,550 | B2 | 11/2004 | Holland et al. |
| 6,843,388 | B1 | 1/2005 | Hollars |
| 6,863,660 | B2 | 3/2005 | Marx |
| 6,939,324 | B2 | 9/2005 | Gonnelli et al. |
| 7,101,862 | B2 | 9/2006 | Chochrum et al. |
| 7,156,880 | B2 | 1/2007 | Evans et al. |
| 7,291,133 | B1 | 11/2007 | Kindler et al. |
| 7,334,598 | B1 | 2/2008 | Hollars |
| 7,534,449 | B2 | 5/2009 | Saltzman et al. |
| 7,544,177 | B2 | 6/2009 | Gertner |
| 7,632,245 | B1 | 12/2009 | Cowan et al. |
| 7,673,783 | B2 | 3/2010 | Morgan et al. |
| 7,691,244 | B2 | 4/2010 | Levitan et al. |
| 7,744,526 | B2 | 6/2010 | McAlister et al. |
| 7,776,822 | B2 | 8/2010 | Terman |
| 7,824,373 | B2 | 11/2010 | Kim |
| 7,857,167 | B1 | 12/2010 | Hollars |
| 2002/0169416 | A1 | 11/2002 | Gonnelli |
| 2003/0023202 | A1 | 1/2003 | Nielson et al. |
| 2003/0108511 | A1 | 6/2003 | Sawhney |
| 2003/0170250 | A1 | 9/2003 | Ezrin et al. |
| 2003/0181917 | A1* | 9/2003 | Gertner ............ 606/82 |
| 2003/0216695 | A1 | 11/2003 | Yang |
| 2005/0070848 | A1 | 3/2005 | Kim et al. |
| 2005/0205087 | A1 | 9/2005 | Kablik et al. |
| 2006/0002852 | A1 | 1/2006 | Saltzman et al. |
| 2006/0052295 | A1 | 3/2006 | Terman |
| 2006/0286664 | A1 | 12/2006 | McAllister et al. |
| 2007/0240989 | A1 | 10/2007 | Levitan et al. |
| 2007/0241119 | A1 | 10/2007 | Durkin et al. |
| 2008/0027272 | A1 | 1/2008 | Kadykowski |
| 2009/0234374 | A1 | 9/2009 | Gabel et al. |
| 2009/0234380 | A1 | 9/2009 | Gabel et al. |
| 2009/0248056 | A1 | 10/2009 | Gabel et al. |
| 2010/0121261 | A1* | 5/2010 | Kablik et al. ............ 604/58 |
| 2010/0137796 | A1 | 6/2010 | Perry et al. |
| 2010/0305505 | A1 | 12/2010 | Ducharme et al. |

FOREIGN PATENT DOCUMENTS

| | | |
|---|---|---|
| DE | 3024749 A1 | 2/1982 |
| DE | 3108918 A1 | 9/1982 |
| DE | 3613762 A1 | 11/1987 |
| EP | 308269 A1 | 3/1989 |
| EP | 0738498 A1 | 10/1996 |
| FR | 2863503 | 12/2003 |
| GB | 10563 A | 0/1896 |
| GB | 1254534 A | 11/1971 |
| JP | 4022109 B | 4/1992 |
| SU | 978999 | 12/1982 |
| WO | WO85/02346 | 6/1985 |
| WO | WO92/20312 | 11/1992 |
| WO | WO94/28798 | 12/1994 |
| WO | WO96/25190 | 8/1996 |
| WO | WO96/37245 | 11/1996 |
| WO | WO96/40327 | 12/1996 |
| WO | WO97/20585 | 6/1997 |
| WO | WO02/053014 | 7/2002 |
| WO | WO2004/073863 | 9/2004 |
| WO | WO2005/100980 | 10/2005 |
| WO | WO2008/008845 | 1/2008 |
| WO | WO2008/023545 | 2/2008 |

OTHER PUBLICATIONS

Response to Office Action for U.S. Appl. No. 12/435,574 filed Nov. 3, 2010, 10 pgs.
Office Action dated Feb. 17, 2011 for U.S. Appl. No. 12/435,574, 8 pgs.
Response to Office Action for U.S. Appl. No. 12/435,574 filed May 13, 2011, 12 pgs.
Office Action dated Aug. 22, 2011 for U.S. Appl. No. 12/435,574, 9 pgs.
Response to Office Action for U.S. Appl. No. 12/435,574 filed Nov. 22, 2011, 11 pgs.
Office Action dated Mar. 30, 2012 for U.S. Appl. No. 12/435,574, 9 pgs.
Response to Office Action for U.S. Appl. No. 12/435,574 filed Aug. 30, 2012, 11 pgs.
Restriction Requirement dated May 25, 2012 for U.S. Appl. No. 12/633,027, 7 pgs.
Response to Restriction Requirement filed Jul. 2, 2012 for U.S. Appl. No. 12/633,027, 7 pgs.
Office Action dated Apr. 14, 2011 for U.S. Appl. No. 12/787,796, 9 pgs.
Response to Office Action filed Jul. 14, 2011 for for U.S. Appl. No. 12/787,796, 11 pgs.
Notice of Allowance dated Oct. 18, 2011 for U.S. Appl. No. 12/787,796, 10 pgs.
International Search Report and Written Opinion for PCT/US2009/067076, mailed Apr. 14, 2010, 23 pgs.
International Search Report and Written Opinion for PCT/US2010/036381, mailed Aug. 20, 2010, 16 pgs.
International Preliminary Report on Patentability for PCT/US2009/042781, mailed Nov. 18, 2010, 11 pgs.
International Search Report completed Sep. 22, 2009 for PCT/US2009/042781, 7 pgs.
Alto Shooter Catalog, Kaigen, English and Japanese, Jun. 1994, 8 pgs.
Decker, "An Efficient Method for the Application of Avitene Hemostatic Agent", Surgery, Gynecology & Obstetrics, 1991, vol. 172, No. 6, 2 pgs.
Endo-Avitene brochure, Med Chem Products, Inc., date unknown, 4 pgs.
Fagelman, et al. "A Simple Method for Application of Microfibrilar Colagen", Surgery, Gynecology & Obstetrics, Jun. 1980, vol. 150, No. 6, 3 pgs.
Hoshino, et al. "Trans-endoscopic Drug Propulsion Therapy", Diagnostic Endoscopy, 1993, vol. 5, 6 pgs.
Surgical Armamentarium, Copyright 1973 V. Mueller, 3 pgs.
Hoshino, "Transendoscopic Projectile Drug Delivery", Gastroenterologia Japonica, vol. 25, No. 5, Jun. 15, 1990, 1 page.
Park et al., "A randomized comparison of a new flexible bipolar hemostasis forceps designed principally for NOTES versus a conventional surgical laparoscopic bipolar forceps for intra-abdominal vessel sealing in a porcine model", Gastrointestinal Endoscopy 2010, vol. 71, No. 4, pp. 835-841.

(56) References Cited

OTHER PUBLICATIONS

Fritscher-Ravens et al., "Beyond NOTES: randomized controlled study of different methods of flexible endoscopic hemostasis of artificially induced hemorrhage, via NOTES access to the peritoneal cavity", Endoscopy 2009, vol. 41, pp. 29-35.
Final Office Action for U.S. Appl. No. 12/435,574 mailed Feb. 17, 2011, 8 pgs.
Examiner Interview Summary for U.S. Appl. No. 12/435,574 dated Jun. 10, 2011, 3 pgs.
Notice of Appeal for U.S. Appl. No. 12/435,574 filed Aug. 17, 2011, 1 pg.
Notice of Allowance dated Oct. 5, 2012 for U.S. Appl. No. 12/633,027, 9 pgs.
International Preliminary Report on Patentability for PCT/US2009/067076 issued Jun. 29, 2011, 12 pgs.
International Preliminary Report on Patentability for PCT/US2010/036381 issued Nov. 29, 2011, 7 pgs.
Examination Report for Australian Patent Application No. 2009244462 issued Sep. 27, 2012; 4 pgs.
Response to Examination Report for Australian Patent Application No. 2009244462 filed Feb. 19, 2013; 8 pgs.
Examination Report for Canadian Patent Application No. 2,723,183 issued Aug. 17, 2012, 2 pgs.
Response to Examination Report for Canadian Patent Application No. 2,723,183 filed Feb. 11, 2013, 5 pgs.
Examination Report for European Patent Application No. 09743424.5 issued Nov. 14, 2011, 5 pgs.
Response to Examination Report for European Patent Application No. 09743424.5 filed Mar. 14, 2012, 10 pgs.
Examination Report for European Patent Application No. 09743424.5 issued Sep. 5, 2012, 6 pgs.
Response to Examination Report for European Patent Application No. 09743424.5 filed Feb. 22, 2013, 4 pgs.
Office Action for U.S. Appl. No. 13/351,524 issued Oct. 18, 2012, 14 pgs.
Examiner Interview Summary for U.S. Appl. No. 13/351,524 issued Feb. 8, 2013, 4 pgs.
Response to Office Action for U.S. Appl. No. 13/351,524 filed Feb. 12, 2013, 9 pgs.
Final Rejection for U.S. Appl. No. 13/351,524 issued Jun. 14, 2013, 12 pgs.
RCE and Amendment for U.S. Appl. No. 13/351,524 filed Dec. 13, 2013, 10 pgs.
Notice of Allowance for U.S. Appl. No. 13/351,524 issued Jan. 17, 2014, 9 pgs.
Examination Report No. 1 for Australian Patent Application 2010253997 issued Mar. 15, 2013, 3 pgs.
Examiner's Report for Canadian Patent Application 2,763,135 issued May 27, 2013, 3 pgs.
Response to Examiner's Report for Canadian Patent Application 2,763,135 filed Nov. 27, 2013, 8 pgs.
Communication for European Patent Application 10722265.5 dated Jan. 27, 2012, 2 pgs.
Reply to Communication for European Patent Application 10722265.5 filed Jul. 27, 2012, 18 pgs.
International Search Report and Written Opinion for PCT/US2013/075005 dated May 2, 2014, 13 pgs.

* cited by examiner

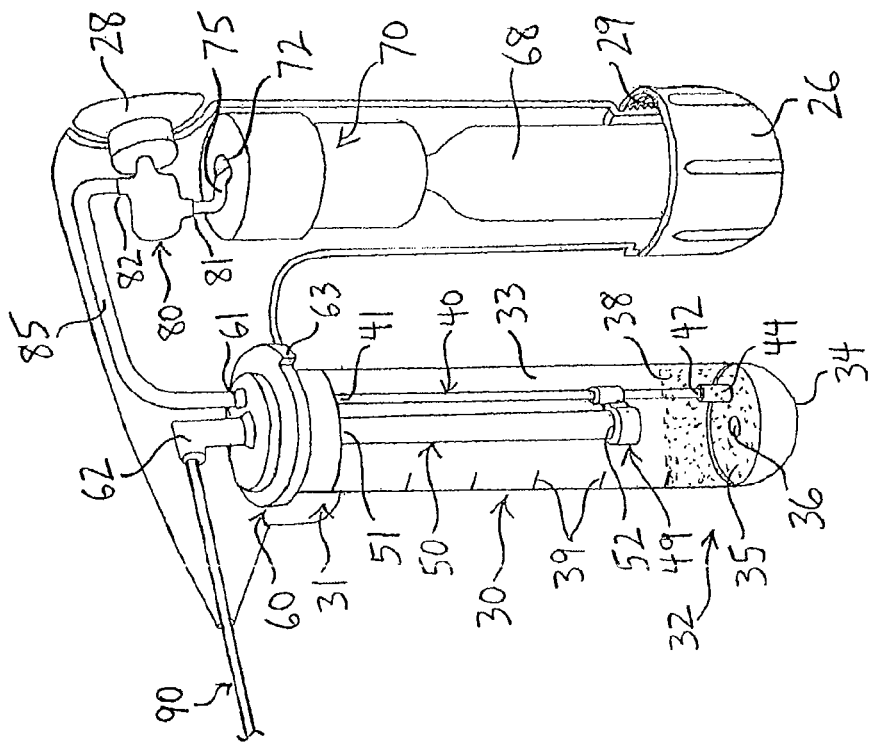
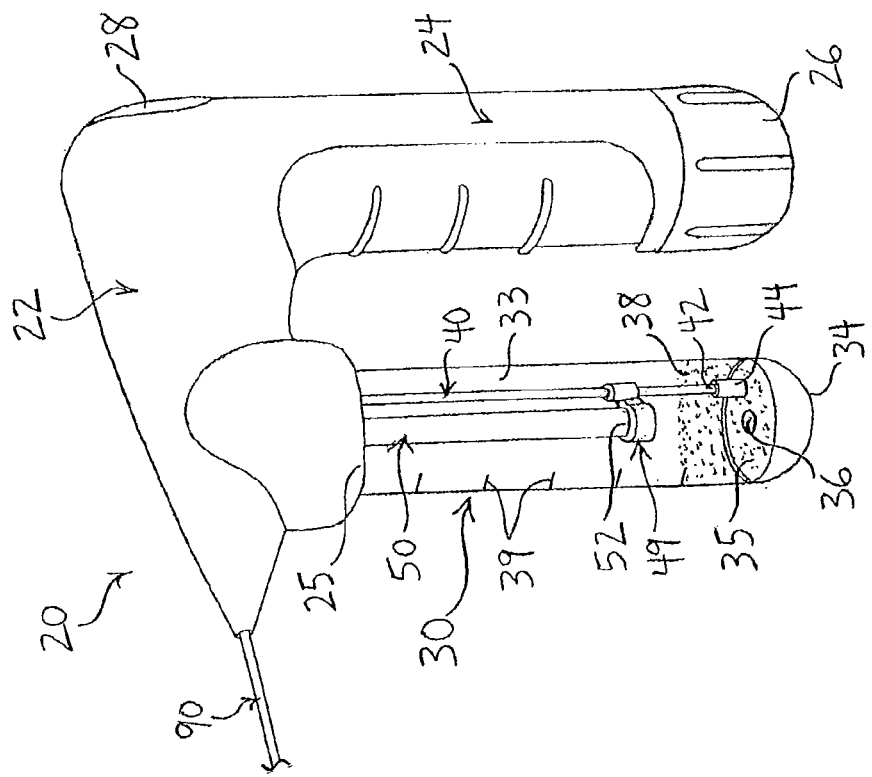
FIG. 1
FIG. 2

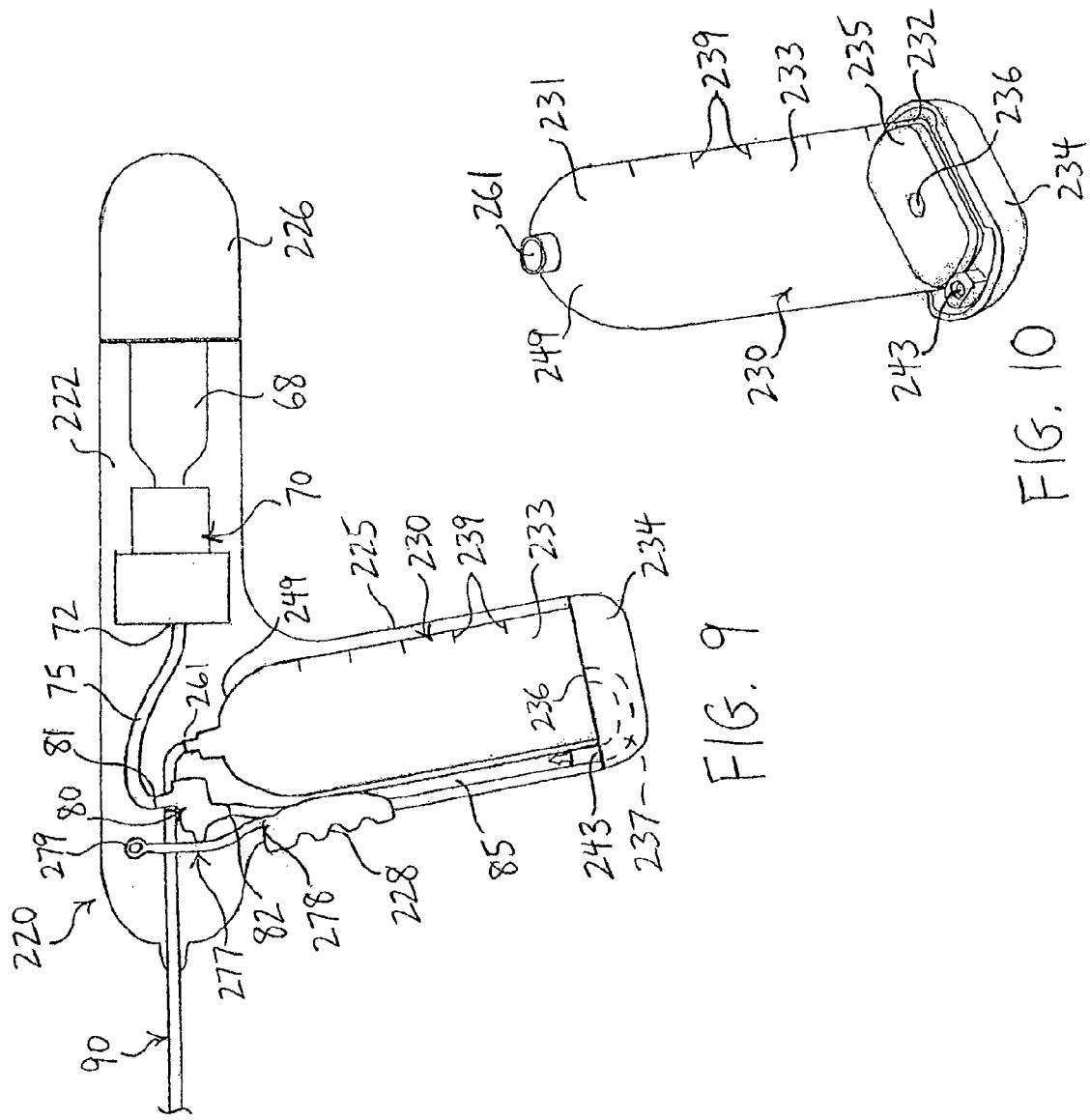
FIG. 9
FIG. 10
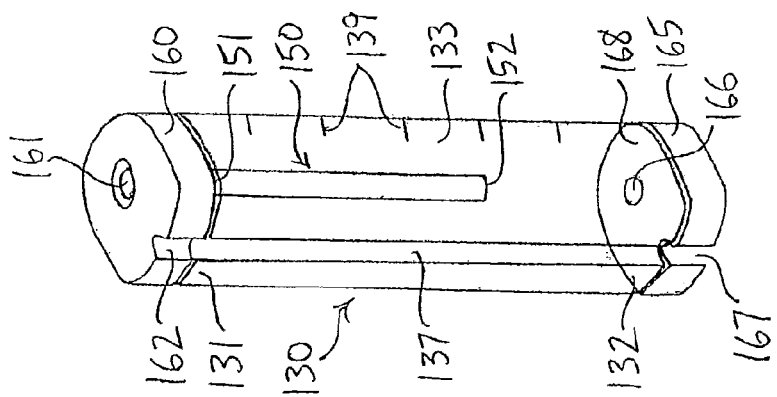
FIG. 8

SYSTEMS AND METHODS FOR DELIVERING THERAPEUTIC AGENTS

PRIORITY CLAIMS

This application is a continuation-in-part of U.S. Utility patent application Ser. No. 13/351,524, filed Jan. 17, 2012, which is a continuation application that claims the benefit of priority under 35 U.S.C. §120 of U.S. patent application Ser. No. 12/787,796, filed May 26, 2010, which claims priority under 35 U.S.C. §119 to U.S. Provisional Patent Application Ser. No. 61/182,463, filed May 29, 2009, each of the foregoing applications are hereby incorporated by reference in their entireties.

BACKGROUND

The present embodiments relate generally to medical devices, and more particularly, to systems and methods for delivering therapeutic agents to a target site.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

SUMMARY

The present embodiments provide systems and methods suitable for delivering a therapeutic agent to a target site. The systems generally comprise a container having first and second regions and a reservoir containing the therapeutic agent. A pressure source having pressurized fluid is in selective fluid communication with at least a portion of the reservoir. An outlet tube is in fluid communication with the reservoir of the container. At least one slot is formed in a lateral surface of the outlet tube at a position between first and second ends of the outlet tube.

The first end of the outlet tube may be disposed closer to a target site and the second end of the outlet tube may be disposed proximal to the first end, and the at least one slot may be positioned closer to the first end than the second end of the outlet tube. In one example, the at least one slot extends between about 45 and about 270 degrees around a perimeter of the outer tube.

In one embodiment, fluid from the pressure source is directed through a first region of the container in a direction towards a second region of the container. The fluid then is at least partially redirected to urge the therapeutic agent in a direction from the second region of the container towards the first region of the container and subsequently towards the target site.

In one embodiment, an inlet tube may be disposed within the container, such that the fluid from the pressure source flows through the inlet tube and into the reservoir of the container. The fluid from the inlet tube may be redirected to then flow in a direction from the second region of the container towards the first region of the container. The outlet tube may be disposed at least partially within the container, wherein fluid exiting the second end of the inlet tube urges the therapeutic agent into the second end of the outlet tube.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a perspective view of a system in accordance with a first embodiment.

FIG. 2 is a schematic view of the system of FIG. 1 with a portion of a housing removed.

FIG. 8 is a perspective view of the container of the system of FIGS. 6-7.

FIG. 9 is a schematic view of a system in accordance with yet a further alternative embodiment with a portion of a housing removed.

FIG. 10 is a perspective view of the container of the system of FIG. 9.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 3:
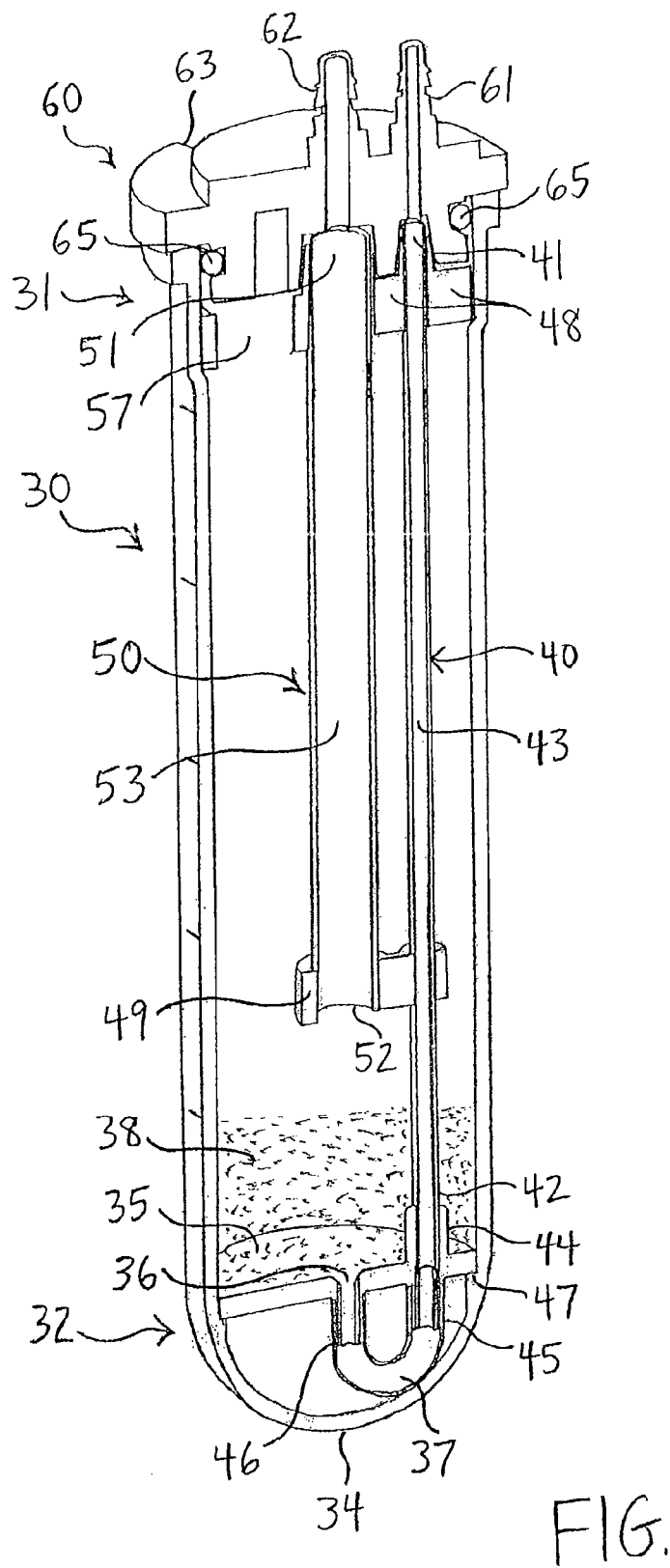
FIG. 3 is a side-sectional view of the container of the system of FIGS. 1-2.

Referring now to FIGS. 1-3, a first embodiment of a system suitable for delivering one or more therapeutic agents is shown. In this embodiment, the system 20 comprises a container 30 that is configured to hold a therapeutic agent 38, and further comprises at least one pressure source 68 that is configured to be placed in selective fluid communication with at least a portion of the container 30, to deliver the therapeutic agent 38 through a catheter 90 to a target site within the patient, as explained more fully below.

The system 20 further comprises a housing 22, which is suitable for securely holding, engaging and/or covering the container 30, pressure source 68, catheter 90, and other components described below. Preferably, the housing 22 comprises an upright section 24 that may be grasped by a user and a section 25 for engaging the container 30. Actuators 26 and 28 may be engaged by a user and selectively operated to perform the functions described below.

The container 30 may comprise any suitable size and shape for holding the therapeutic agent 38. In FIGS. 1-3, the container 30 comprises a generally tube-shaped configuration having a first region 31, a second region 32, and a reservoir 33 defined by an interior of the container 30. A platform 35 may be positioned within the container 30 above a curved end region 34, as best seen in FIG. 3.

The platform 35 preferably forms a substantially fluid tight seal with an inner surface of the container 30, thereby preventing the therapeutic agent 38 that is disposed in the reservoir 33 from reaching an inner portion of the curved end region 34, as shown in FIG. 3. In this embodiment, the platform 35 comprises an opening 36 though which fluid from the pressure source 68 is directed via a u-shaped tube 37 disposed within the curved end region 34, as shown in FIG. 3 and explained in further detail below.

The container 30 may further comprise an inlet tube 40, an outlet tube 50, and a cap 60, wherein the cap 60 is configured to be secured to the first region 31 of the container 30, as depicted in FIG. 3. The inlet tube 40 has first and second ends 41 and 42 with a lumen 43 extending therebetween, while the outlet tube 50 has first and second ends 51 and 52 with a lumen 53 extending therebetween. The first end 41 of the inlet tube 40 is placed in fluid communication with an inlet port 61 formed in the cap 60, while the first end 51 of the outlet tube 50 is placed in fluid communication with an outlet port 62 formed in the cap 60, as shown in FIG. 3.

The second end 42 of the inlet tube 40 extends towards the platform 35, and may be coupled to an adapter 14, which may be integral with the platform 35 or secured thereto. The adapter 44 places the second end 42 of the inlet tube 40 in fluid communication with a first end 45 of the u-shaped tube 37, which is disposed within the curved end region 34, as shown in FIG. 3. A second end 46 of the u-shaped tube 37 is in fluid communication with the opening 36 in the platform 35.

Accordingly, fluid passed through the inlet port 61 of the cap 60 is directed through the inlet tube 40, through the u-shaped tube 37, and into the reservoir 33 via the opening 36. Notably, the u-shaped tube 37 effectively changes the direction of the fluid flow by approximately 180 degrees, such that the fluid originally flows in a direction from the first region 31 of the container 30 towards the second region 32, and then from the second region 32 back towards the first region 31. In the embodiment of FIGS. 1-3, the first region 31 of the container 30 is disposed vertically above the second region 32 of the container 30 during use, however, it is possible to have different placements of the first and second regions 31 and 32 relative to one another, such that they are disposed at least partially horizontally adjacent to one another.

The second end 52 of the outlet tube 50 may terminate a predetermined distance above the platform 35, as shown in FIGS. 1-3. While the second end 52 is shown relatively close to the platform 35 in this embodiment, any suitable predetermined distance may be provided. For example, the outlet tube 50 may be shorter in length, e.g., about half of the length shown in FIGS. 1-3, and therefore, the second end 52 may be spaced apart further from the platform 35. In a presently preferred embodiment, the second end 52 of the outlet tube 50 is radially aligned with the opening 36 in the platform 35, as depicted in FIGS. 1-3. Accordingly, as will be explained further below, when fluid from the pressure source 68 is directed through the opening 36 in the platform 35, the fluid and the therapeutic agent 38 within the reservoir 33 may be directed through the outlet tube 50, through the outlet port 62, and towards a target site. Alternatively, the outlet tube 50 may be omitted and the therapeutic agent 38 may flow directly from the reservoir 33 into the outlet port 62. Other variations on the container 30 and outlet port 62 may be found in U.S. patent application Ser. No. 12/633,027, filed Dec. 8, 2009, which is hereby incorporated by reference in its entirety.

The cap 60 may comprise any suitable configuration for sealingly engaging the first region 31 of the container 30. In one example, an O-ring 65 is held in place around a circumference of the cap 60 to hold the therapeutic agent 38 within the reservoir 33. Further, the cap 60 may comprise one or more flanges 63 that permit a secure, removable engagement with a complementary internal region of the section 25 of the housing 22. For example, by rotating the container 30, the flange 63 of the cap 60 may lock in place within the section 25.

The inlet and outlet tubes 40 and 50 may be held in place within the container 30 by one or more support members. In the example shown, a first support member 48 is secured around the inlet and outlet tubes 40 and 50 near their respective first ends 41 and 51, as shown in FIG. 3. The first support member 48 may be permanently secured around the inlet and outlet tubes 40 and 50, and may maintain a desired spacing between the tubes. Similarly, a second support member 49 may be secured around the inlet and outlet tubes 40 and 50 near their respective second ends 42 and 52, as shown in FIGS. 1-3. As will be apparent, greater or fewer support members may be provided to hold the inlet and outlet tubes 40 and 50 in a desired orientation within the container 30. For example, in one embodiment, the second support member 49 may be omitted and just the first support member 48 may be provided, or greater than two support members may be used.

In a loading technique, the inlet and outlet tubes 40 and 50 may be securely coupled to the first support member 48, the second support member 49, the platform 35 and the u-shaped tube 37. The platform 35 may be advanced towards the second region 32 of the empty container 30 until the platform rests on a step 47 above the curved end region 35 of the container 30, as shown in FIG. 3. In a next step, a desired quantity of the therapeutic agent 38 may be loaded through slits 57 formed adjacent to, or within, the first support member 48, as depicted in FIG. 3. Notably, the container 30 also may comprise measurement indicia 39, which allow a user to determine a quantity of the therapeutic agent 38 that is loaded within the reservoir 33 as measured, for example, from the top of the platform 35. With the therapeutic agent 38 loaded into the reservoir 33, the cap 60 may be securely coupled to the first region 31 of the container 30, and the container 30 then is securely coupled to the section 25 of the handle 22 as described above.

The pressure source 68 may comprise one or more components capable of producing or furnishing a fluid having a desired pressure. In one embodiment, the pressure source 68 may comprise a pressurized fluid, such as a liquid or gas. For example, as shown in FIG. 2, the pressure source 68 may comprise a pressurized fluid cartridge of a selected gas or liquid, such as carbon dioxide, nitrogen, or any other suitable gas or liquid that may be compatible with the human body. The pressurized fluid cartridge may contain the gas or liquid at a relatively high, first predetermined pressure, for example, around 1,800 psi inside of the cartridge. The pressure source 68 optionally may comprise one or more commercially available components. The pressure source 68 therefore may comprise original or retrofitted components capable of providing a fluid or gas at an original pressure.

The fluid may flow from the pressure source 68 through a pressure regulator, such as regulator valve 70 having a pressure outlet 72, as depicted in FIG. 2, which may reduce the pressure to a lower, second predetermined pressure. Solely by way of example, the second predetermined pressure may be in the range of about 30 to about 80 psi, although any suitable pressure may be provided for the purposes described below.

The actuator 26 may be actuated to release the fluid from the pressure source 68. For example, a user may rotate the actuator 26, which translates into linear motion via a threaded engagement 29 between the actuator 26 and the housing 22, as shown in FIG. 2. When the linear advancement is imparted to the pressure source 68, the regulator valve 70 may pierce through a seal of the pressure cartridge to release the high pressure fluid. After the regulator valve 70 reduces the pressure, the fluid may flow from the pressure outlet 72 to an actuation valve 80 via tubing 75.

The actuation valve 80 comprises an inlet port 81 and an outlet port 82. The actuator 28, which may be in the form of a depressible button, may selectively engage the actuation valve 80 to selectively permit fluid to pass from the inlet port 81 to the outlet port 82. For example, the actuation valve 80 may comprise a piston having a bore formed therein that permits fluid flow towards the outlet port 82 when the actuator 28 engages the actuation valve 80. Fluid that flows through the outlet port 82 is directed into the inlet port 61 of the cap 60 via tubing 85, and subsequently is directed into the container 30, as explained above. It will be appreciated that any suitable coupling mechanisms may be employed to secure the various pieces of tubing to the various valves and ports.

The system 20 further may comprise one or more tube members for delivering the therapeutic agent 38 to a target site. For example, the tube member may comprise a catheter 90 having a proximal end that may be placed in fluid communication with the outlet port 62. The catheter 90 further comprises a distal end that may facilitate delivery of the therapeutic agent 38 to a target site. The catheter 90 may comprise a flexible, tubular member that may be formed from one or more semi-rigid polymers. For example, the catheter may be manufactured from polyurethane, polyethylene, tetrafluoroethylene, polytetrafluoroethylene, fluorinated ethylene propylene, nylon, PEBAX or the like. Further details of a suitable tube member are described in U.S. application patent Ser. No. 12/435,574 ("the '574 application"), filed May 5, 2009, the disclosure of which is hereby incorporated by reference in its entirety. As explained further in the '574 application, a needle suitable for penetrating tissue may be coupled to the distal end of the catheter 90 to form a sharp, distal region configured to pierce through a portion of a patient's tissue, or through a lumen wall to perform a translumenal procedure.

In operation, the distal end of the catheter 90 may be positioned in relatively close proximity to the target site. The catheter 90 may be advanced to the target site using an open technique, a laparoscopic technique, an intraluminal technique, using a gastroenterology technique through the mouth, colon, or using any other suitable technique. The catheter 90 may comprise one or more markers configured to be visualized under fluoroscopy or other imaging techniques to facilitate location of the distal end of the catheter 90. If desired, the catheter 90 may be advanced through a working lumen of an endoscope.

When the catheter 90 is positioned at the desired target site, the pressure source 68 may be actuated by engaging the actuator 26. As noted above, the pressurized fluid may flow from the pressure source 68 through a regulator valve 70 and be brought to a desired pressure and rate. The fluid then flows through the tubing 75, and when the actuator 28 is selectively depressed, the fluid flows through the valve 80 and through the tubing 85 towards the container 30. The fluid is then directed through the inlet port 62, through the inlet tube 40 within the container 30, and through the u-shaped tube 37. At this point, the u-shaped tube effectively changes the direction of the fluid flow. Regulated fluid then flows through the opening 36 in the platform 35 and urges the therapeutic agent 38 through the outlet tube 50. The fluid and the therapeutic agent 38 then exit through the first end 51 of the outlet tube 50, through the outlet port 62 of the cap 60, and through the catheter 90, thereby delivering the therapeutic agent 38 to the target site at a desired pressure.

Optionally, a control mechanism may be coupled to the system 20 to variably permit fluid flow into and/or out of the container 30 at a desired time interval, for example, a predetermined quantity of fluid per second. In this manner, pressurized fluid may periodically flow into or out of the container 30 periodically to deliver the therapeutic agent 38 to a target site at a predetermined interval or otherwise periodic basis.

The system 20 may be used to deliver the therapeutic agent 38 in a wide range of procedures and the therapeutic agent 38 may be chosen to perform a desired function upon ejection from the distal end of the catheter 90. Solely by way of example, and without limitation, the provision of the therapeutic agent 38 may be used for providing hemostasis, closing perforations, performing lithotripsy, treating tumors and cancers, treat renal dialysis fistulae stenosis, vascular graft stenosis, and the like. The therapeutic agent 38 can be delivered during procedures such as coronary artery angioplasty, renal artery angioplasty and carotid artery surgery, or may be used generally for treating various other cardiovascular, respiratory, gastroenterology or other conditions. The above-mentioned systems also may be used in transvaginal, umbilical, nasal, and bronchial/lung related applications.

For example, if used for purposes of hemostasis, thrombin, epinephrine, or a sclerosant may be provided to reduce localized bleeding. Similarly, if used for closing a perforation, a fibrin sealant may be delivered to a localized lesion. In addition to the hemostatic properties of the therapeutic agent 38, it should be noted that the relatively high pressure of the fluid and therapeutic agent, by itself, may act as a mechanical tamponade by providing a compressive force, thereby reducing the time needed to achieve hemostasis.

The therapeutic agent 38 may be selected to perform one or more desired biological functions, for example, promoting the ingrowth of tissue from the interior wall of a body vessel, or alternatively, to mitigate or prevent undesired conditions in the vessel wall, such as restenosis. Many other types of therapeutic agents 38 may be used in conjunction with the system 20.

The therapeutic agent 38 may be delivered in any suitable form. For example, the therapeutic agent 38 may comprise a powder, liquid, gel, aerosol, or other substance. Advantageously, the pressure source 68 may facilitate delivery of the therapeutic agent 38 in any one of these forms.

The therapeutic agent 38 employed also may comprise an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the therapeutic agent 38 may include thrombolytic agents used to dissolve blood clots that may adversely affect blood flow in body vessels. A thrombolytic agent is any therapeutic agent that either digests fibrin fibers directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

In one example, the therapeutic agent 38 comprises a hemostasis powder manufactured by TraumaCure, Inc. of Bethesda, Md. However, while a few exemplary therapeutic agents 38 have been described, it will be apparent that numerous other suitable therapeutic agents may be used in conjunction with the system 20 and delivered through the catheter 90.

Advantageously, the system 20 permits localized delivery of a desired quantity of the therapeutic agent 38 at a desired, regulated pressure. Since the distal end of the catheter 90 may be placed in relatively close proximity to a target site, the system 20 provides significant advantages over therapeutic agents delivered orally or through an IV system and may reduce accumulation of the therapeutic agent 38 in healthy tissues, thereby reducing side effects. Moreover, the delivery of the therapeutic agent 38 to the target site is performed in a relatively fast manner due to the relatively high pressure of the fluid, thereby providing a prompt delivery to the target site compared to previous devices.

Further, if an optional needle is employed at the distal end of the catheter 90, as explained in the '574 application, the system 20 advantageously may be used to both perforate tissue at or near a target site, then deliver the therapeutic agent 38 at a desired pressure in the manner described above. For example, the needle may comprise an endoscopic ultrasound (EUS) needle. Accordingly, in one exemplary technique, a sharpened tip of the needle may be capable of puncturing through an organ or a gastrointestinal wall or tissue, so that the therapeutic agent 38 may be delivered at a predetermined pressure in various bodily locations that may be otherwise difficult to access. One or more delivery vehicles, such as an endoscope or sheath, may be employed to deliver the catheter 90 to a target site, particularly if the distal end of the catheter 90 comprises the optional needle.

Figure 5:
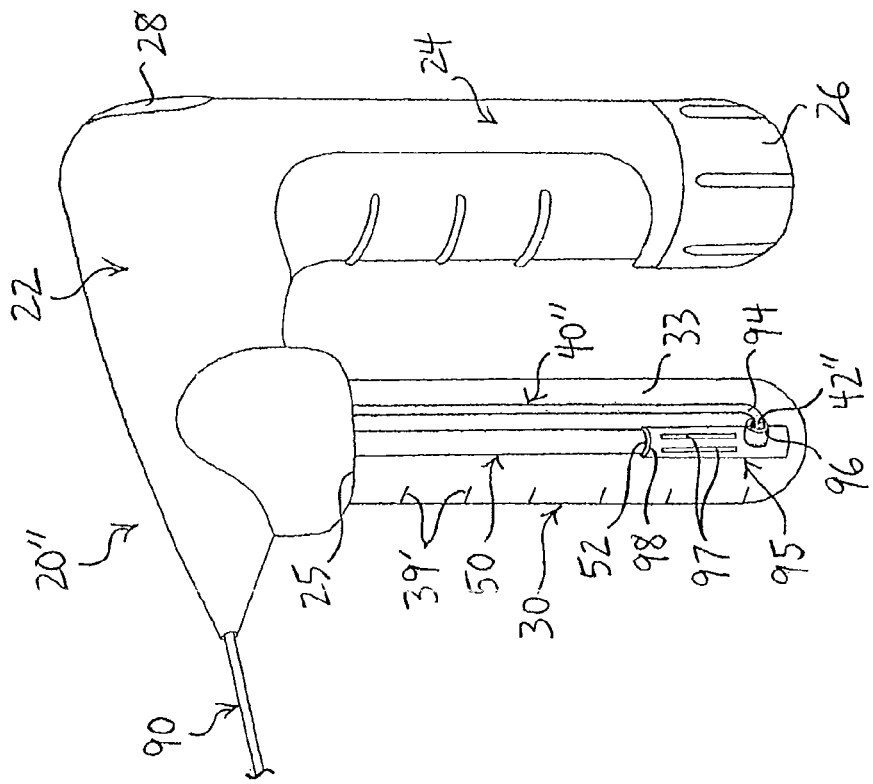
FIG. 5 is a perspective view of a system in accordance with a further alternative embodiment.
Figure 4:
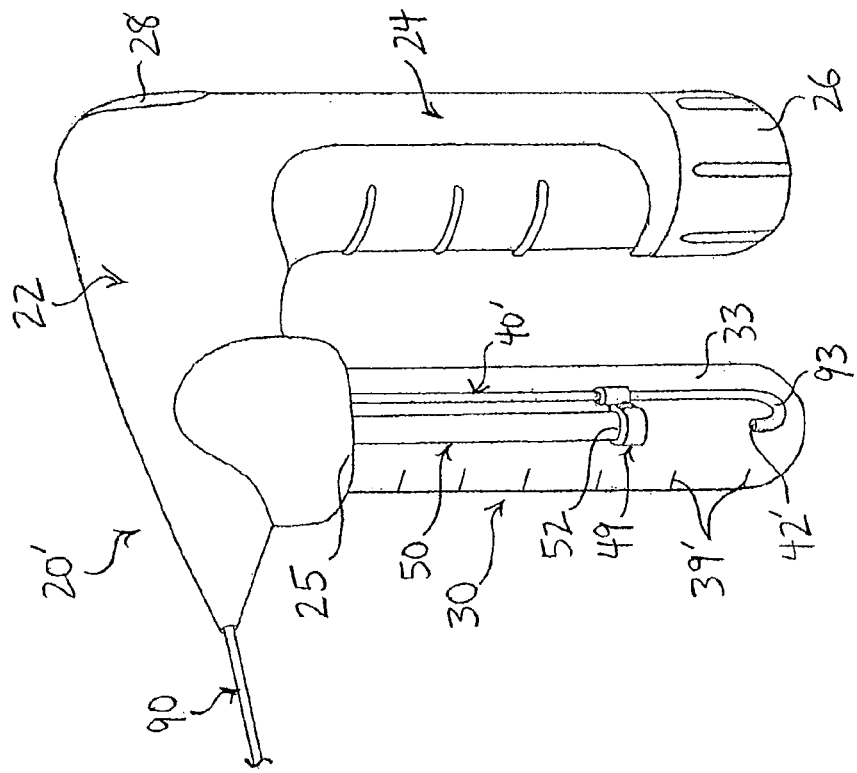
FIG. 4 is a perspective view of a system in accordance with an alternative embodiment.

Referring now to FIGS. 4-5, alternative systems 20' and 20" are similar to the system 20 of FIGS. 1-3, with main exceptions noted below. In FIG. 4, the alternative system 20' comprises an inlet tube 40' having a J-shaped curvature 93 that causes a second end 42' of the inlet tube 40' to direct fluid flow in a substantially opposing direction relative to the first end 41 of the inlet tube 40'. In use, fluid from the pressure source 68 flows through the first end 41 of the inlet tube 40', through the J-shaped curvature 93 and exits the second end 42', thereby directing the therapeutic agent 38 (not shown in FIG. 4) into the outlet tube 50 for delivery to a target site via the catheter 90, as generally explained above. In this embodiment, the platform 35 may be omitted and the therapeutic agent 38 may settle on a lower region of the reservoir 33. Measurement indicia 39' may measure a quantity of the therapeutic agent 38 from the lower region of the reservoir 33.

In the embodiment of FIG. 4, as well as FIGS. 1-3, a filter may cover the second end 52 of the outlet tube 50. The filter may be sized to ensure that only relatively small particles of the therapeutic agent 38 enter into the outlet tube 50, thereby reducing the risk of clogging. If relatively large particles become present in the reservoir 33, the fluid from the pressure source 68 entering into the container may break up the larger particles until they are small enough to pass through the filter and into the outlet tube 50.

In FIG. 5, the alternative system 20" comprises an inlet tube 40" having a curvature 94 that directs fluid into a flow assembly 95. The flow assembly 95 has an inlet 96 comprising at least one bore configured for fluid communication with the second end 42" of the inlet tube 40". The flow assembly 95 further comprises an outlet 98 that is coupled to, and in fluid communication with, the second end 52 of the outlet tube 50. At least one opening 97 is formed in a lateral surface of the flow assembly 95 between the inlet 96 and the outlet 98, wherein the openings 97 are sized to permit suctioning of the therapeutic agent 38 therethrough. The openings 97 may comprise slits, as generally depicted, or alternatively circular bores or other shapes. In use, fluid from the pressure source 68 flows through the first end 41 of the inlet tube 40", through the curvature 94 and the second end 42", and into the flow assembly 95 via the inlet 96. The fluid thereby directs the therapeutic agent 38 within the reservoir 33 into the outlet tube 50, via the openings 97, for delivery to a target site via the catheter 90.

In particular, as fluid from the pressure source 68 passes from the inlet 96 to the outlet 98, a localized low pressure system will be provided in the vicinity of the openings 97 in accordance with Bernoulli's principle of fluid dynamics. The low pressure system formed by the presence of the pressurized fluid passing through the flow assembly 95 will form a strong suction force when it passes by the openings 97. As a result, the therapeutic agent 38 may be suctioned out of the reservoir 33, through the openings 97 and through the outlet 98 and outlet tube 50. Notably, the slits or other openings may be sized to ensure that only relatively small particles of the therapeutic agent 38 enter into the outlet tube 50, thereby reducing the risk of clogging.

Figure 7:
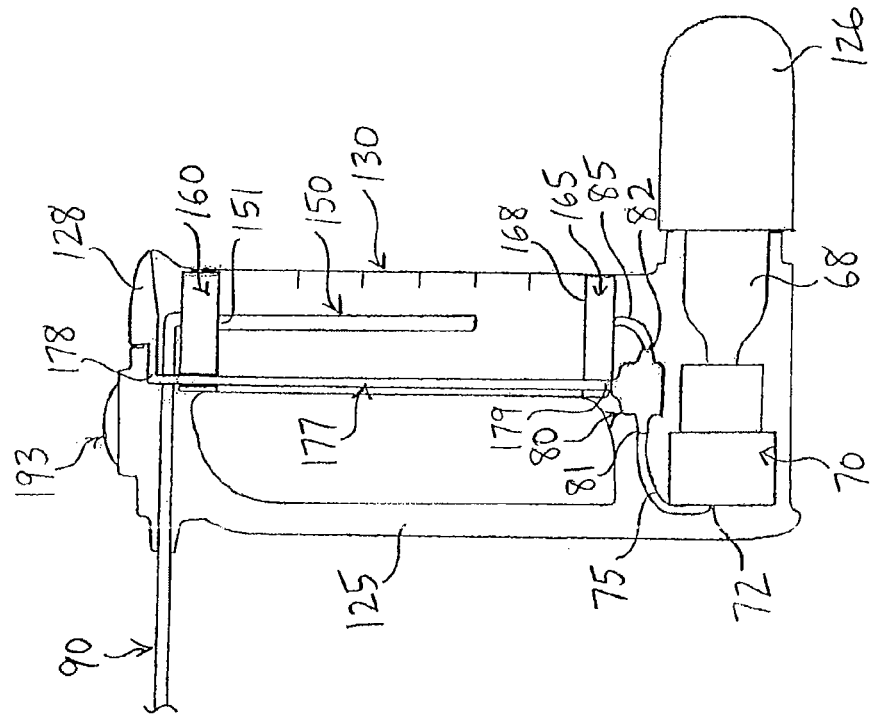
FIG. 7 is a schematic view of the system of FIG. 6 with a portion of a housing removed.
Figure 6:
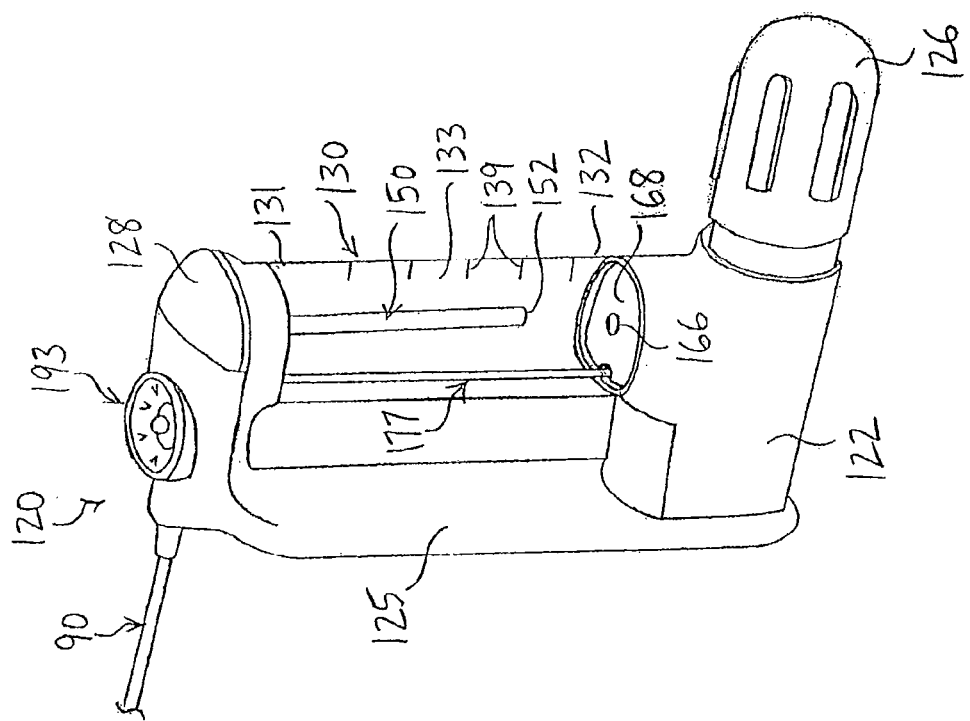
FIG. 6 is a perspective view of a system in accordance with yet a further alternative embodiment.

Referring now to FIGS. 6-8, a system 120 according to an alternative embodiment is described. The system 120 comprises a housing 122, which is suitable for securely holding, engaging and/or covering the components described below. A user may hold the system 120 during use by grasping an upright support 125 and/or an outer surface of a container 130. Actuators 126 and 128, which are similar to actuators 26 and 28 above, may be engaged by a user and actuated to perform the functions described below.

The container 130 may comprise any suitable size and shape for holding the therapeutic agent 38 described above (not shown in FIGS. 6-8 for illustrative purposes). The container 130 has a first region 131 and a second region 132. An upper cap 160 may securely engage the first region 131, while a lower cap 165 may securely engage the second region 132, thereby holding the therapeutic agent 38 within a reservoir 133. Measurement indicia 139 are provided to determine a quantity of the therapeutic agent 38 within the reservoir 133.

In this embodiment, an outlet tube 150 having first and second ends 151 and 152 is positioned within the container 130. The second end 152 of the tube 150 terminates a predetermined distance above an upper surface 168 of the lower cap 165, as shown in FIGS. 6-8. Further, the second end 152 of the outlet tube 150 may be aligned with an opening 166 in the upper surface 168 of the lower cap 165, as depicted in FIGS. 6 and 8.

The system 120 further comprises at least one linkage 177 having first and second ends 178 and 179. The first end 178 of the linkage 177 is coupled to the actuator 128, while the second end 179 of the linkage 177 is coupled to the valve 80. Accordingly, when the actuator 128 is depressed, the valve 80 may be selectively actuated. The container 130 may comprise a groove 137, as best seen in FIG. 8, for accommodating the linkage 177. The upper and lower caps 160 and 165 also may comprise corresponding grooves 162 and 167, respectively, for accommodating the linkage 177. It will be apparent that any number of linkages may be used, and their positioning within the housing 122 may be varied, as needed, to impart a desired motion from the actuator 128 to selectively actuate the valve 80.

Optionally, an orientation device 193 may be used for indicating a vertical orientation of the container 130. The orientation device 193 may be formed integrally with the housing 122, or coupled to an exterior surface of the housing 122. The orientation device 193 may comprise a captive liquid, ball, arrow or other member, or an electronic display, which provides an indication of the vertical orientation of the container 130. Therefore, when the system 120 is held in a user's hand, the user may determine whether the container 130 is oriented vertically, which may enhance flow of the therapeutic agent 38 and other functionality. Notably, the orientation device 193 shown in FIGS. 6-7 also may be used in the embodiments of FIGS. 1-5 and 8-9.

Operation of the system 120 is similar to the operation of the system 20 described above. After the catheter 90 is positioned at a desired location, the pressure source 68 may be actuated by engaging the actuator 126. As noted above, the pressurized fluid may flow through a regulator valve 70 and be brought to a desired pressure and rate. The fluid then flows through the tubing 75, and when the actuator 28 is selectively actuated, the fluid flows through the valve 80 and through the tubing 85 towards the container 130. Regulated fluid then flows through the opening 166 within the lower cap 165, into the reservoir 133, and urges the therapeutic agent 38 through the outlet tube 150 in a direction from the second end 152 towards the first end 151. The fluid and the therapeutic agent 38 then exit through the first end 151 of the outlet tube 150, through the opening 161 of the upper cap 160, and through the catheter 90, which is in fluid communication with the opening 161. Accordingly, the therapeutic agent 38 is delivered to the target site at a desired interval and pressure.

Referring now to FIGS. 9-10, a system 220 according to a further alternative embodiment is described. The system 220 comprises a housing 222, which is suitable for securely holding, engaging and/or covering the components described below. A user may hold the system 220 during use by grasping a generally upright support 225. Actuators 226 and 228, which are similar to actuators 26 and 28 above, may be engaged by a user and actuated to perform the functions described below.

In this embodiment, an alternative container 230 comprises a reservoir 233 for holding the therapeutic agent 38 described above (not shown in FIGS. 9-10 for illustrative purposes). The container 230 has a first region 231 and a second region 232. Measurement indicia 239 are provided to determine a quantity of the therapeutic agent 38 within the reservoir 233.

In this embodiment, the second region 232 of the container 230 is securely coupled to a lower cap 234. The lower cap 234 comprises an inlet port 243, which is in fluid communication with an opening 236 formed in an upper surface 235 of the lower cap 234. A flexible u-shaped tube 237 may be coupled between the inlet port 243 and the opening 236 to provide fluid communication therebetween, as depicted in FIG. 9.

The system 220 further comprises at least one linkage 277 having first and second ends 278 and 279. The first end 278 of the linkage 277 is coupled to the actuator 228, while the second end 279 of the linkage 277 may be pivotable about an inner element of the housing 222. For example, the second end 279 may comprise a bore, as shown in FIG. 9, which may be secured around a prong (not shown) extending within the housing 222, thereby allowing the second end 279 to pivot around the prong. Accordingly, when the actuator 228 is depressed, a central region of the linkage 277 may engage the valve 80 to selectively actuate the valve and permit flow therethrough. As will be apparent, any number of linkages may be used, and their positioning within the housing 222 may be varied, as needed, to impart a desired motion from the actuator 228 to selectively actuate the valve 80.

Operation of the system 220 is similar to the operation of the system 20 described above. After the catheter 90 is positioned at a desired location, the pressure source 68 may be actuated by engaging the actuator 226. As noted above, the pressurized fluid may flow through a regulator valve 70 and be brought to a desired pressure and rate. The fluid then flows through the tubing 75, and when the actuator 228 is selectively actuated, the fluid flows through the valve 80 and through the tubing 85. Fluid then flows through the inlet port 243, through the u-shaped tube positioned within the lower cap 234, through the opening 236 and into the reservoir 233. Fluid entering the reservoir 233 then urges the therapeutic agent 38 through an outlet port 261 at the first region 231 of the container 230. The first region 231 may comprise a curve or taper 249 to direct the fluid and the therapeutic agent 38 through the opening 261. Subsequently, the fluid and the therapeutic agent 38 flow through the catheter 90, which is in fluid communication with the opening 261, thereby delivering the therapeutic agent 38 to the target site at a desired pressure.

As noted above, in alternative embodiments the outlet tubes 50 and 150 of FIGS. 1-5 and 6-8, respectively, may be omitted. Therefore, fluid entering into the reservoirs 33 and 133 may urge the therapeutic agent 38 in a direction through outlet port in the caps 60 and 160. A taper or curve may be provided to guide the therapeutic agent 38 out of the containers 30 and 130.

Figure 11:
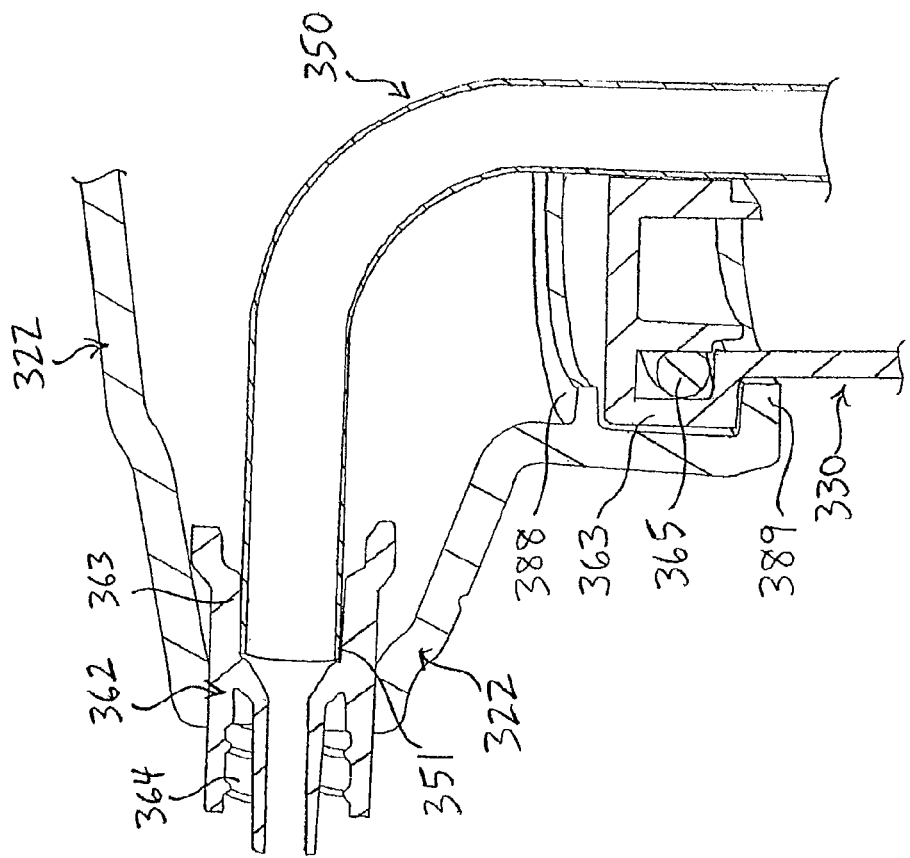
FIG. 11 is a side-sectional view of a portion of a system in accordance with an alternative embodiment.

Referring to FIG. 11, in an alternative embodiment, an outlet tube 350 has a first end 351 that is coupled to an outlet port 362 formed in a distal tip of the housing 322. The outlet port 362 has proximal and distal regions 363 and 364, whereby the proximal region 363 is configured to securely engage the first end 351 of the outlet tube 350, and the distal region 364 is configured to be coupled to the catheter 90 of FIGS. 1-2. A luer-type connection may be provided. Advantageously, by disposing the outlet tube 350 near the distal tip of the housing, and exposed to a user via a luer-type connection, a physician may easily exchange the catheter 90 during a procedure, for example, if the catheter 90 becomes occluded.

Further, FIG. 11 depicts an alternative connection of a container 330 to the housing 322. The container 330 is similar to the container 30 described above, but in the embodiment of FIG. 11, a cap of the container 330 comprises a flanged region 363 having an O-ring 365 disposed therein, wherein the flanged region 363 is configured to be secured between upper and lower internal stops 388 and 389 of the housing 322. In this manner, the flanged region 363 of the cap may be held in place without the ability to be removed, thereby permanently securing the container 330 to the handle 322 and eliminating the opportunity for the container 330 to be reusable. Notably, other features of the cap of FIG. 11 that are not shown may be provided in a manner similar to the cap 60 of FIG. 3, such as the inlet port 61.

Figure 12:
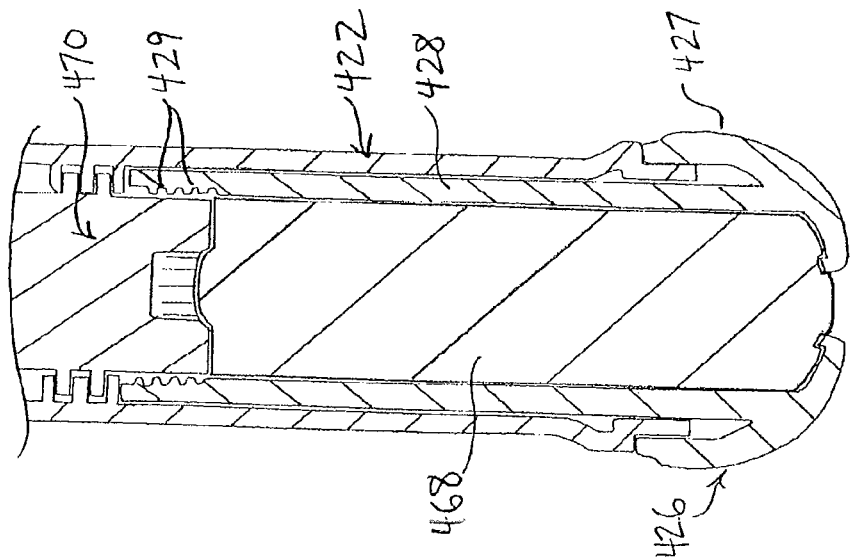
FIG. 12 is a side-sectional view of an alternative actuator arrangement.

Referring to FIG. 12, an alternative actuator 426 is provided, which is generally similar to the actuator 26 of FIGS. 1-2, with a main exception that there is provided a lower handle portion 427 and a generally upright portion 428 that extends vertically within the housing 422 and upwards beyond a portion of a regulator valve 70. An upper region of the generally upright portion 428 comprises threading 429, which is configured to engage threading on an outer surface of the regulator valve 70.

In use, a user may rotate the lower handle portion 427 of the actuator 426, which translates into linear motion relative to the regulator valve 470 via the threaded engagement 429. When the linear advancement is imparted to a pressure source 468 in a chamber, the regulator valve 470 may pierce through a seal of the pressure cartridge to release the high pressure fluid. After the regulator valve 470 reduces the pressure, the fluid may flow from the pressure outlet 72 to an actuation valve 80 via tubing 75, in the manner explained in FIG. 2 above. Optionally, a safety ledge or interference may be provided on the housing 422 to prevent the actuator 426 from becoming disengaged, which could otherwise allow the pressure cartridge to be ejected from the device.

Figure 14:
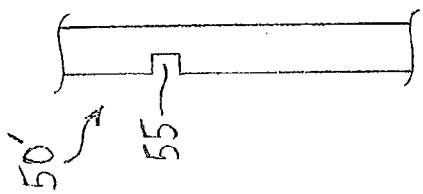
FIG. 14 is a side view illustrating a section of the alternative outlet tube of FIG. 13.
Figure 13:
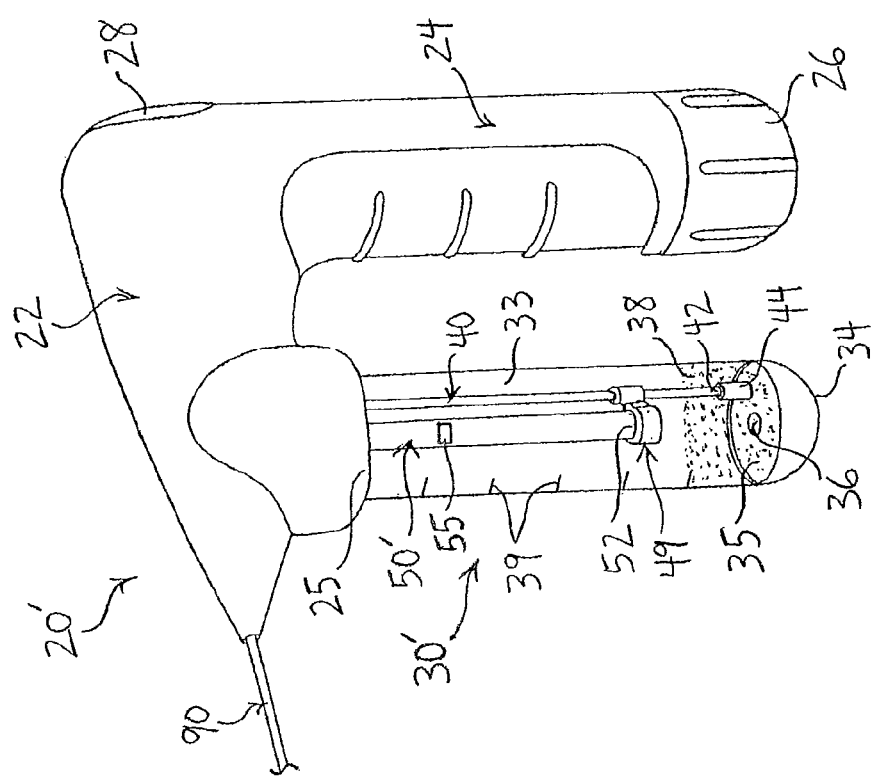
FIG. 13 is a perspective view of a system in accordance with an alternative outlet tube relative to the embodiment of FIG. 1.

Referring now to FIGS. 13-14, a system 20' for delivering a therapeutic agent is similar to system 20 of the embodiment of FIGS. 1-3, with a main exception that an alternative outlet tube 50' comprises at least one slot 55 formed in a lateral surface of the outlet tube 50'. The slot 55 is formed in the lateral surface at a location between the first and second ends 51 and 52 of the outlet tube 50'. The slot 55 provides an area of communication between the lumen 53 (shown in FIG. 3 above) of the outlet tube and the reservoir 33 defined by an interior of the container 30'.

In one embodiment, the slot 55 extends between about 45 and about 270 degrees around a perimeter of the outlet tube 50', as depicted in FIGS. 13-14. In one example, the slot 55 may be positioned at a location closer to the first end 51 than the second end 52, as depicted in FIG. 13. Further, while one slot 55 is shown in FIGS. 13-14, it is possible that multiple slots may be formed in a lateral surface of the outlet tube 50', at locations that are axially spaced apart and/or circumferentially offset from the slot 55 depicted in FIG. 13. The location of the slot 55 that is depicted in FIG. 13 is not intended to be limiting.

Advantageously, the inventor has surprisingly discovered that the provision of the at least one slot 55 may reduce the incidence of the device "burping" the therapeutic agent 38 after the actuator 28 is disengaged by the operator. Furthermore, the provision of the slot 55 may reduce the amount of the therapeutic agent 38 that is left in the catheter 90 that can cause the catheter 90 to clog when it is in contact with blood.

More specifically, when the actuator 28 is engaged by the operator, the fluid from the pressure source 68 is allowed to enter the reservoir 33 holding the therapeutic agent 38 to enable delivery of the therapeutic agent 38 to a target site, as described above. It has been discovered that some pressure builds up in the reservoir 33 when the actuator 28 is engaged. When the operator disengages the actuator 28, there is still some pressure in the reservoir 33. In the absence of the slot 55, the therapeutic agent 38 can fall to the bottom of the reservoir 33 due to gravity, and then the pressurized fluid from regions above within the reservoir 33 may push a "burp" of the therapeutic agent 38 from the device as the fluid pressure is reduced. It has been found that this can leave some of the therapeutic agent 38 within the catheter 90, which can cause clogging. Moreover, an operator may unexpectedly find that some of the therapeutic agent 38 is still being deployed from the catheter 90, even after they have disengaged actuation of the actuator 28.

By placing the at least one slot 55 in a lateral surface of the outlet tube 50', the aforementioned potential drawbacks can be avoided. For example, in an embodiment in which the slot 55 is positioned closer to the first end 51 than the second end 52, i.e., higher up when used in a generally vertical orientation as depicted in FIG. 13, then instead of forcing the therapeutic agent 38 that has settled down in the reservoir 33 out of the catheter 90 when some pressure remains in the reservoir 33, the pressurized fluid itself can exit the reservoir 33 via the slot 55 near the top of the outlet tube 50'. This action has been found to effectively purge the catheter 90 with substantially only the pressurized fluid, thereby reducing the instance of "burping" with the therapeutic agent 38 and catheter clogging by the therapeutic agent 38.

It will be appreciated that while the at least one slot 55 has been shown as being disposed in a lateral surface of the outlet tube 50' in a modified version of the embodiment of FIGS. 1-3, at least one slot may be provided in any of the outlet tubes of the alternative embodiments described herein, i.e., besides the embodiment of FIGS. 1-3.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system suitable for delivering a therapeutic agent to a target site, the system comprising:
    a container for holding the therapeutic agent, wherein the container comprises first and second regions and has a reservoir containing the therapeutic agent;

a pressure source having pressurized fluid, the pressure source in selective fluid communication with at least a portion of the reservoir of the container;

an outlet tube in fluid communication with the reservoir of the container;

at least one slot formed in a circumferential surface of the outlet tube at a position between first and second ends of the outlet tube; and an inlet tube disposed within the container, the inlet tube having a first end positioned near the first region of the container and a second end positioned near the second region of the container, wherein the fluid from the pressure source flows through the inlet tube in the direction from the first region to the second region and into the reservoir of the container.

2. The system of claim 1, wherein fluid from the pressure source is directed through the first region of the container in a direction towards the second region of the container, and wherein the fluid is at least partially redirected to urge the therapeutic agent in a direction from the second region of the container towards the first region of the container and subsequently towards the target site.

3. The system of claim 1, where the first end of the outlet tube is disposed closer to a target site and the second end of the outlet tube is disposed proximal to the first end, where the at least one slot is positioned closer to the first end than the second end of the outlet tube.

4. The system of claim 1 where the at least one slot extends between about 45 and about 270 degrees around a perimeter of the outlet tube.

5. The system of claim 1 wherein, during use, the first region of the container is disposed vertically above the second region of the container.

6. The system of claim 1 further comprising a cap secured to the first region of the container, the cap having an inlet port and an outlet port, wherein the fluid from the pressure source is directed through the inlet port of the cap, and wherein the fluid is redirected within the container to urge the therapeutic agent through the outlet port of the cap.

7. The system of claim 1 wherein the outlet tube is disposed at least partially within the container, wherein fluid exiting the second end of the inlet tube urges the therapeutic agent into the second end of the outlet tube and towards the first end of the outlet tube.

8. The system of claim 7 wherein the second end of the outlet tube is spaced away from the second end of the inlet tube.

9. The system of claim 1 further comprising a platform positioned within the container, the platform forming a substantially fluid tight seal with an inner surface of the container, wherein the therapeutic agent is retained above the platform.

10. The system of claim 1 wherein the therapeutic agent comprises a powder.

11. A system suitable for delivering a therapeutic agent to a target site, the system comprising:

a container for holding the therapeutic agent, wherein the container comprises first and second regions and has a reservoir containing the therapeutic agent;

a pressure source having pressurized fluid, the pressure source in selective fluid communication with at least a portion of the reservoir of the container;

an outlet tube in fluid communication with the reservoir of the container;

at least one slot formed in a circumferential surface of the outlet tube at a position between first and second ends of the outlet tube; and a platform positioned within the container, the platform forming a substantially fluid tight seal with an inner surface of the container, wherein the therapeutic agent is retained above the platform, wherein the slot is closer to the target site relative to the platform.

12. The system of claim 11, wherein fluid from the pressure source is directed through the first region of the container in a direction towards the second region of the container, and wherein the fluid is at least partially redirected to urge the therapeutic agent in a direction from the second region of the container towards the first region of the container and subsequently towards the target site.

13. The system of claim 11, where the first end of the outlet tube is disposed closer to a target site and the second end of the outlet tube is disposed proximal to the first end, where the at least one slot is positioned closer to the first end than the second end of the outlet tube.

14. The system of claim 11 where the at least one slot extends between about 45 and about 270 degrees around a perimeter of the outlet tube.

15. The system of claim 11 wherein, during use, the first region of the container is disposed vertically above the second region of the container.

16. The system of claim 11 further comprising a cap secured to the first region of the container, the cap having an inlet port and an outlet port, wherein the fluid from the pressure source is directed through the inlet port of the cap, and wherein the fluid is redirected within the container to urge the therapeutic agent through the outlet port of the cap.

17. The system of claim 11 further comprising an inlet tube disposed within the container, the inlet tube having a first end positioned near the first region of the container and a second end positioned near the second region of the container, wherein the fluid from the pressure source flows through the inlet tube in the direction from the first region to the second region and into the reservoir of the container.

18. The system of claim 17 wherein the outlet tube is disposed at least partially within the container, wherein fluid exiting the second end of the inlet tube urges the therapeutic agent into the second end of the outlet tube and towards the first end of the outlet tube.

19. The system of claim 18 wherein the second end of the outlet tube is spaced away from the second end of the inlet tube.

20. The system of claim 11 wherein the therapeutic agent comprises a powder.

* * * * *